United States Patent
Scott et al.

(10) Patent No.: US 9,618,469 B2
(45) Date of Patent: Apr. 11, 2017

(54) SENSING WATER VAPOUR

(75) Inventors: Graeme Scott, Maynooth County (IE); Richard Coull, Dundalk (IE); Vittorio Scardaci, Dublin (IE)

(73) Assignee: Hewlett-Packard Development Company, L.P., Houston, TX (US)

( * ) Notice: Subject to any disclaimer, the term of this patent is extended or adjusted under 35 U.S.C. 154(b) by 399 days.

(21) Appl. No.: 14/240,362

(22) PCT Filed: Sep. 19, 2011

(86) PCT No.: PCT/US2011/052108
§ 371 (c)(1),
(2), (4) Date: Feb. 22, 2014

(87) PCT Pub. No.: WO2013/043148
PCT Pub. Date: Mar. 28, 2013

(65) Prior Publication Data
US 2014/0182372 A1    Jul. 3, 2014

(51) Int. Cl.
*G01N 27/12*     (2006.01)
*B05D 3/02*      (2006.01)
*G01N 25/02*     (2006.01)

(52) U.S. Cl.
CPC ......... *G01N 27/121* (2013.01); *B05D 3/0254* (2013.01); *G01N 25/02* (2013.01); *G01N 27/127* (2013.01)

(58) Field of Classification Search
CPC .... B05D 3/0254; G01N 25/02; G01N 27/121; G01N 27/127
See application file for complete search history.

(56) References Cited

U.S. PATENT DOCUMENTS

| | | | |
|---|---|---|---|
| 4,898,476 A * | 2/1990 | Herrmann | G01N 25/68 324/664 |
| 7,067,098 B2 | 6/2006 | Colbert et al. | |
| 7,270,002 B2 | 9/2007 | Chen et al. | |
| 7,972,699 B2 | 7/2011 | Rinzler et al. | |
| 2002/0143232 A1 * | 10/2002 | Richards | A61G 11/00 600/22 |

(Continued)

FOREIGN PATENT DOCUMENTS

| IN | 00297DE2008 A | 9/2009 |
|---|---|---|
| IN | 01732DE2009 A | 2/2011 |
| WO | WO-2010016024 | 2/2010 |

OTHER PUBLICATIONS

Liu et al., Humidity Sensitivity of Multi-Walled Carbon Nanotube Networks Depoisted by Dielectrophoresis; Sensors (ISSN 1424-8220); Jan. 22, 2009; pp. 1-8.

(Continued)

*Primary Examiner* — Hezron E Williams
*Assistant Examiner* — David Z Huang
(74) *Attorney, Agent, or Firm* — Dierker & Kavanaugh, P.C.

(57) ABSTRACT

A water vapor sensor comprises a substrate and a film of carbon nanotubes impregnated with surfactant on the substrate. The substrate is of material which is inert relative to the film. Two or more electrical conductors are in contact with in spaced apart zones of the film, whereby the impedance of the film may be measured. The sensor is housed in housing which protects the sensor but also allows exposure of the film to water vapor.

14 Claims, 10 Drawing Sheets

(56) References Cited

U.S. PATENT DOCUMENTS

| | | |
|---|---|---|
| 2005/0186333 A1 | 8/2005 | Douglas |
| 2005/0269285 A1 | 12/2005 | Jung et al. |
| 2007/0153363 A1 | 7/2007 | Gruner |
| 2009/0112115 A1 | 4/2009 | Huang et al. |
| 2010/0102281 A1* | 4/2010 | Hisashi ............ B82Y 30/00 252/511 |

OTHER PUBLICATIONS

Lu et al., Chemo-sensitivity of Latex-based Films Containing Segregated Networks of Carbon Nanotubes, Sicence Direct, vol. 155, Issue 1, Jul. 5, 2011, pp. 28-26.

Parikh et al., Flexible Vapour Sensors Using Single Walled Carbon Nanotubes, Sensors and Actuators B Chemical 113, Jan. 20, 2005, pp. 55-63.

Zahab et al., Water-Vapor Effect on the Electrical Conductivity of a Single-Walled Carbon Nanotube Mat, Physical Review B, vol. 62, No. 15, Oct. 15, 2000.

* cited by examiner

SENSING WATER VAPOUR

FIELD

The present invention relates to water vapour sensor and a method of making such a sensor. An embodiment of the invention relates to a humidity sensor. Another embodiment relates to a dew point sensor.

BACKGROUND

Water vapour sensors, in particular humidity sensors, also known as hygrometers, are well known. Hygrometers are used for many purposes: meteorology; monitoring environments within buildings; controlling air conditioning; in industry; making paper; horticulture; monitoring foodstuffs in supply chains; and many other uses.

Humidity is difficult to measure. Many techniques for measuring humidity are based on relatively large physical sensors. Small electronic sensors are used but such sensors are based on semiconductor techniques: and require semiconductor production facilities. For example it is known to combine carbon nanotubes with field effect transistors for sensing humidity.

DETAILED DESCRIPTION OF ILLUSTRATIVE EMBODIMENTS OF THE INVENTION

Figure 1:
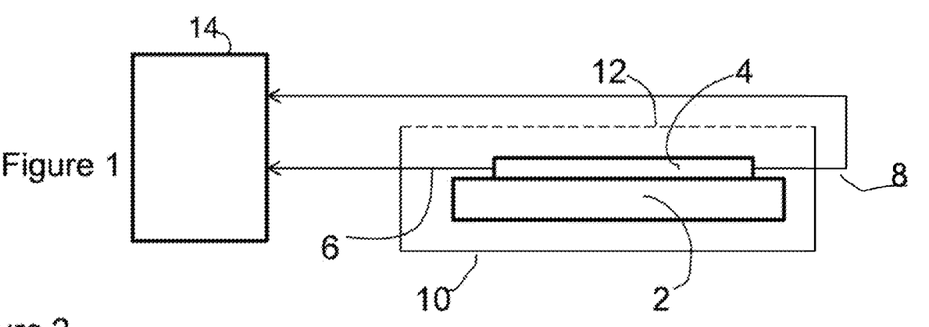
FIG. 1 is a schematic diagram of a water vapour sensor in accordance with the invention.

Referring to FIG. 1, the water vapour sensor comprises a substrate 2 on which is a film 4 of carbon nanotubes impregnated with surfactant. Electrical conductors 6 and 8 are connected to spaced apart zones 60, 80 (shown in FIG. 3) of the film. Surfactant maybe removed from the zones. The sensor is in a housing 10, which protects the film, substrate and conductors but which allows water vapour (e.g. humid air) to enter the housing. The housing mechanically protects the film from damage which may change its resistance. The housing may for example have holes in a wall 12 above the film. A sheet (not shown) porous to humid air may cover the holes inside the housing. An example of a suitable sheet is a thin film with micro perforations. The housing may be of plastics or any other suitable material which mechanically protects the film, and does not absorb water vapour. Plastics may be chosen because they are also electrically insulative.

A measuring device 14 may be connected to the conductors 6, 8 to measure the resistance of the film. The measured resistance is a measure of the amount of water vapour.

The carbon nanotubes may be single walled tubes or multiwalled tubes or a mixture of single and multiwalled tubes. The carbon nanotubes are a mixture of metallic and semiconductive tubes.

The surfactant may be sodium dodecyl sulphate (SDS) or any other suitable surfactant Other suitable surfactants include SDBS (sodium dodecyl benzene sulfonate), CTAB (Hexadecyl Trimethyl Ammonium Bromide), and polyethylene glycol p-(1,1,3,3-tetramethylbutyl)-phenyl ether, which may be sold as Triton X-100 (Trade Mark).

The substrate may be of plastics, ceramic glass, silicon, paper for example photo-paper, or any other suitable material which is inert to the film. The substrate may be rigid or flexible. The substrate may be transparent. A suitable substrate is PET (Polyethylene terephthalate), which is flexible and transparent.

The measuring device is an ohmmeter: such devices are well known.

Figure 3:
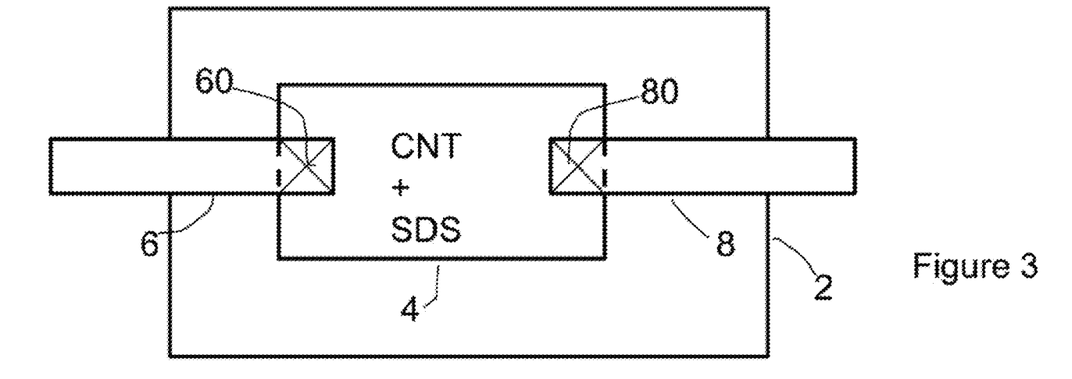
FIG. 3 is a plan view of a part of the water vapour sensor of FIG. 1.

One example of the water vapour sensor comprises a film 4 of single walled carbon nanotubes impregnated with SDS deposited on a flexible sheet 2 of transparent PET. The carbon nanotube film of this example of the sensor is also transparent. The film may be about 100 nm thick. The conductors 6 and 8 make contact with silver paste deposited on the spaced apart zones 60, 80 of the film. In this example all surfactant is removed from the zones, but is not removed outside the zones.

Figure 2:
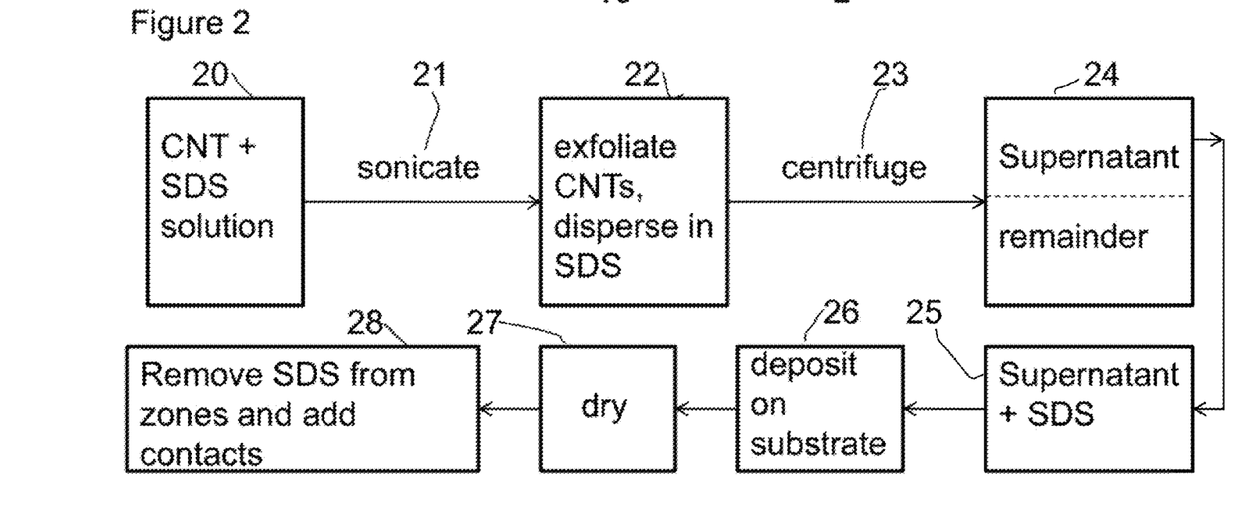
FIG. 2 is a block diagram of an illustrative method of making the water vapour sensor of FIG. 1.

Referring to FIG. 2, a method of making the sensor comprises depositing carbon nanotubes impregnated with, and wet with, surfactant on an inert substrate, drying the impregnated tubes to form a film of impregnated tubes on the substrate, and connecting spaced apart zones of the film to electrical conductors. An example of the method comprises the following steps.

The process starts with single walled carbon nanotubes in dry powder form. The carbon nanotubes are put 20 in a solution of SDS in deionized (DI) water containing a concentration of SDS above the critical micelle concentration: for example a dispersion of 0.1% wt SWNT and 1% SDS in DI water. The mixture of carbon nanotubes and SDS is sonicated 21 to produce an exfoliated dispersion 22 which is centrifuged 23 to produce a supernatant 24 and a remainder. The supernatant and SDS associated with the supernatant is separated 25 from the remainder. The supernatant and SDS is then deposited 26 as a film on a substrate, in this example a sheet of PET, by fluid jet printing, spray deposition or dip coating. Other deposition techniques may be used. The deposited film is then dried 27.

Surfactant is not removed: instead it is incorporated in the water vapour sensor. The presence of surfactant has been found to greatly increase the sensitivity of the water vapour sensor as compared to a similar sensor but in which all surfactant has been removed.

In one example, the carbon nanotubes are sprayed onto a PET film placed on a hot plate. Temperatures up to the glass transition point of PET can be used. In one example, the plate is held at 70° C. The deposited film has a thickness of for example 100 nm. In step 28, SDS is removed from the spaced apart zones 60, 80 (see FIG. 3) of the film and conductive contacts applied to the zones. The SDS may be removed from the zones by applying a mask to the carbon nanotube film to protect the film outside the zones and applying DI water to the zones. SDS may be removed from the zones by using a fluid jet printer to apply DI water to the zones.

FIG. 3 is a plan view of a carbon nanotube film 4 having spaced apart zones 60, 80 from which surfactant has been removed and conductive contacts applied, the contacts overlapping the edge of the film onto the substrate 2. The conductive contacts may be silver paste or any other suitable conductor compatible with carbon nanotubes and the substrate.

The resistance of the film may be measured using the known four point measurement which eliminates contributions from contact resistance: see for example http://en.wikipedia.org/wiki/Four terminal sensing. In the case of four point measurement it is not strictly necessary to remove the SDS from the area of the electrical contact points on the carbon nanotube film.

The method of FIG. 2 provides a straightforward method of making a humidity sensor in which a carbon nanotube film is provided by simple deposition techniques.

Figure 4:
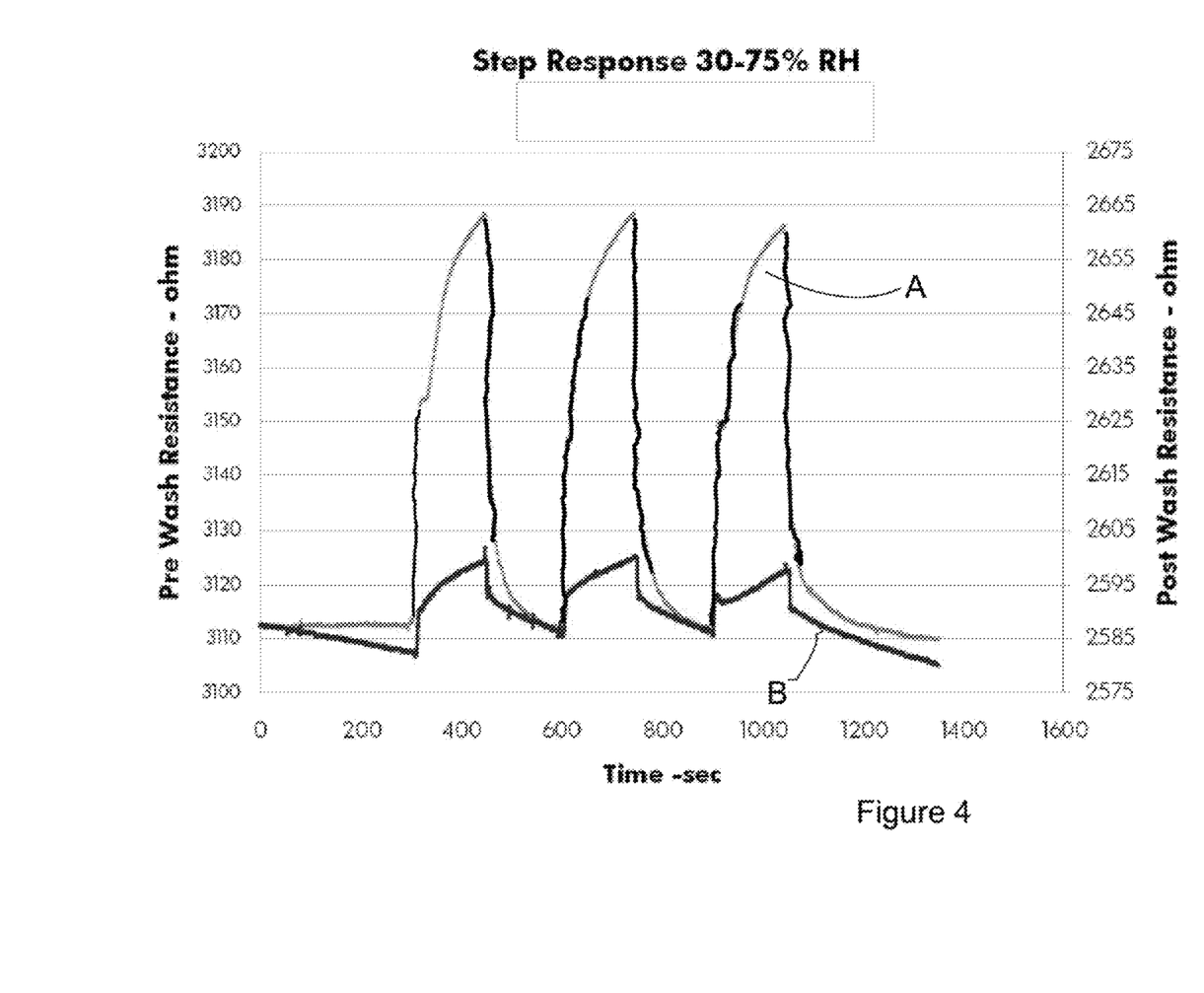
FIG. 4 is a graph showing the response to humidity change of the sensor of FIG. 1 compared to a different form of sensor.
Figure 5:
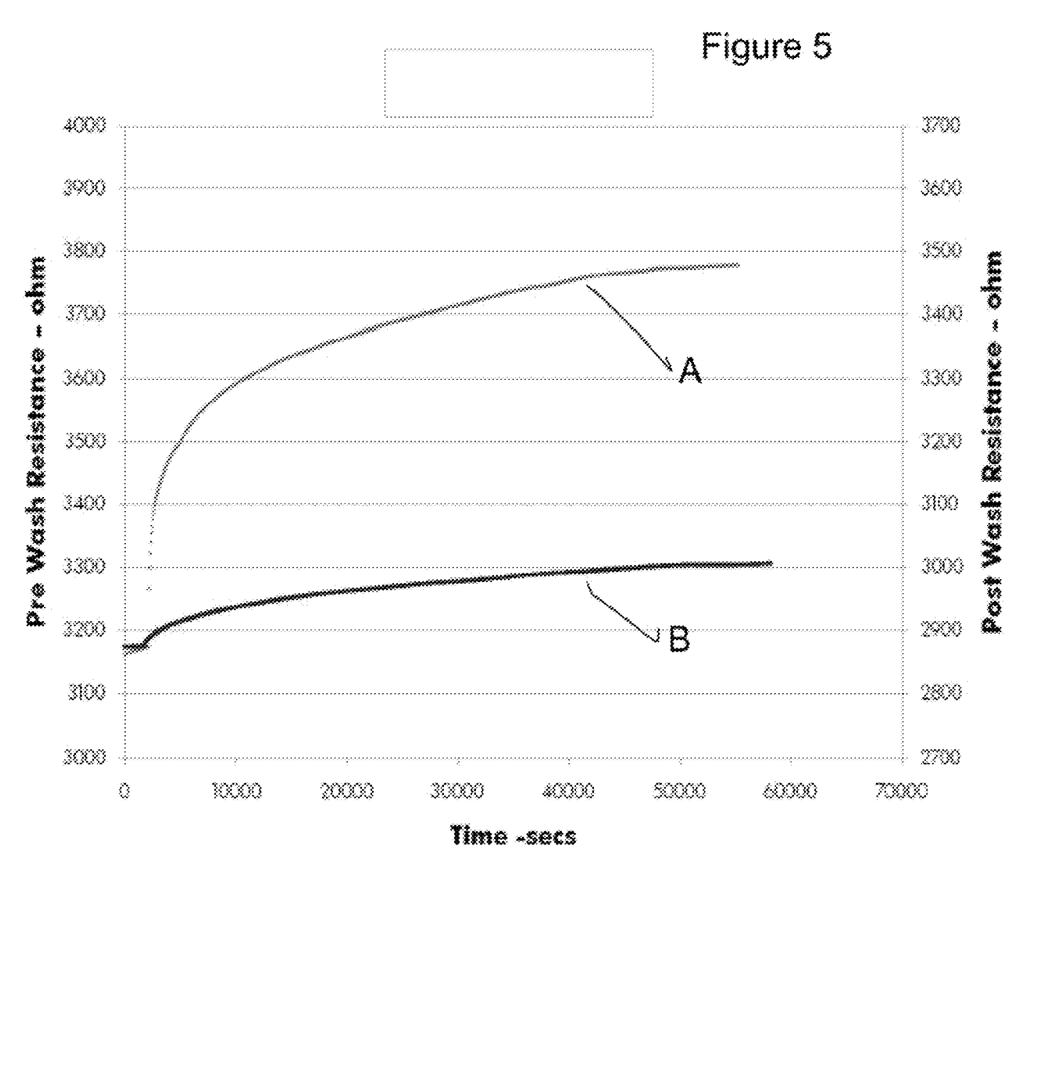
FIG. 5 is a graph showing the change of resistance to a step change in humidity of the sensor of FIG. 1.

By not removing SDS, the carbon nanotubes deposited in the substrate are impregnated with the SDS. As shown in FIGS. 4 and 5, it has been found that the SDS increases the sensitivity A of the resistance of the carbon nanotubes to water vapour (humidity) compared to a sensor B in which the SDS is removed.

The graph of FIG. 4 compares changes in the resistance A of SWNT films (measured with a Keithley 2400 Source Meter) exposed to varying relative humidity levels when the films remain impregnated with SDS surfactant with the resistance B when the SDS is removed. The graph shows the change in film resistivity when repeatedly switching relative humidity from about 30% (lab level) to about 75% at constant temperature. Although the shapes of the curves are complex, the increased sensitivity with the SDS impregnated film (line A) is clear.

The graph of FIG. 5 shows the change in film resistance in response to a single step change in relative humidity from about 30% (lab level) to about 75%. Both curves A and B show very long response times, but again the higher sensitivity of the SDS impregnated film (line A) compared to the resistance (B) of film having no SDS is clear.

Figure 6:
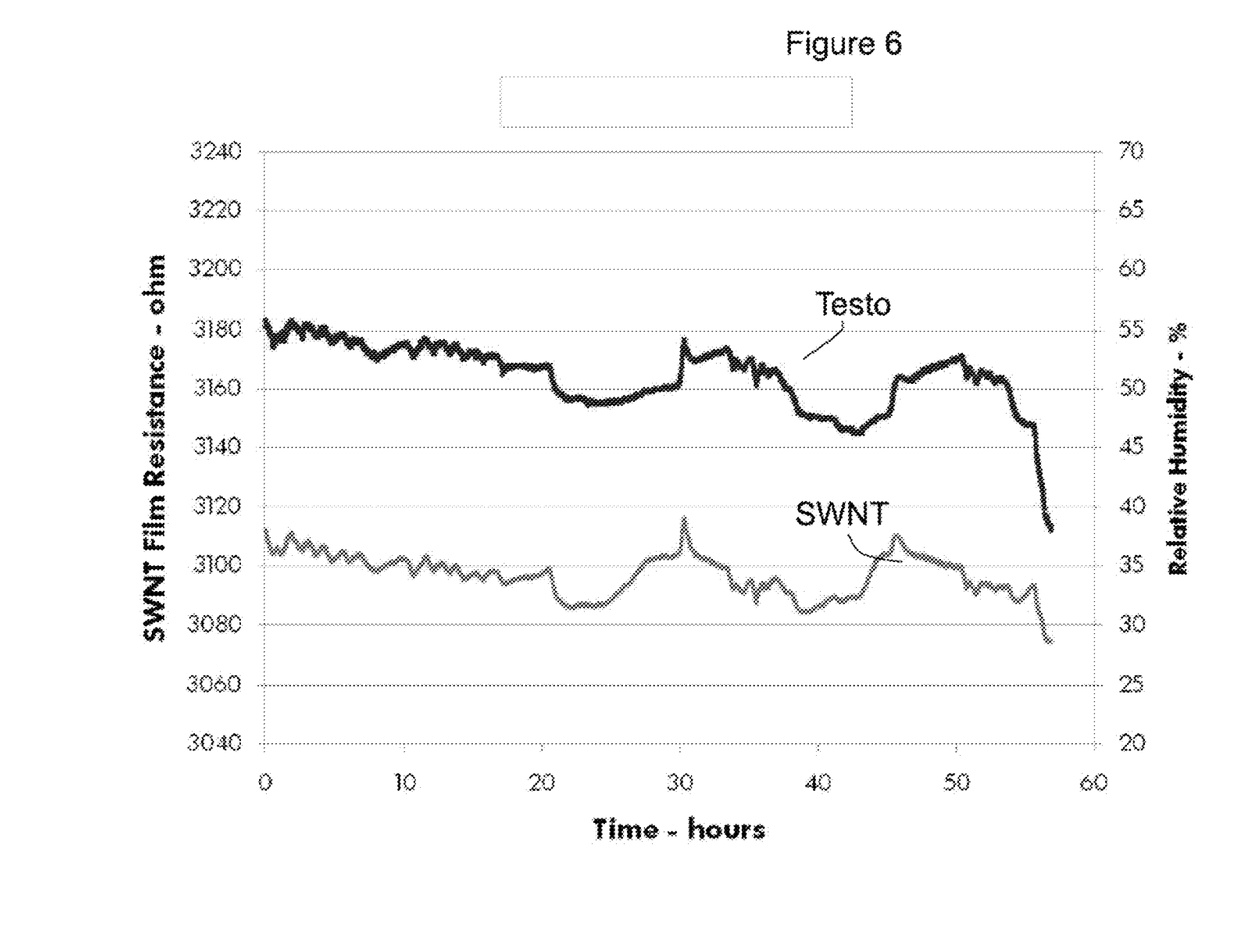
FIG. 6 is a graph comparing the response of the sensor of FIG. 1 compared to a Testo 174H sensor.

The graph of FIG. 6 charts the changes of resistance of an SDS impregnated SWNT film in response to natural changes in lab relative humidity over several days (blue curve). The reference relative humidity measurement was made with a Testo 174H data logger (red curve). Over the course of this test the lab temperature remained constant at 18.5° C.

Whilst the water vapour sensor of FIG. 1 provides a measure of water vapour, its resistance is also dependent on temperature The sensor of FIG. 1 does not measure relative humidity. The sensor of FIG. 1 may include a temperature sensor for use in compensating for variation of resistance with temperature without measuring relative humidity.

A humidity sensor which measures relative humidity requires a measure of temperature because the saturation pressure of water vapour in air depends on temperature.

Figure 7:
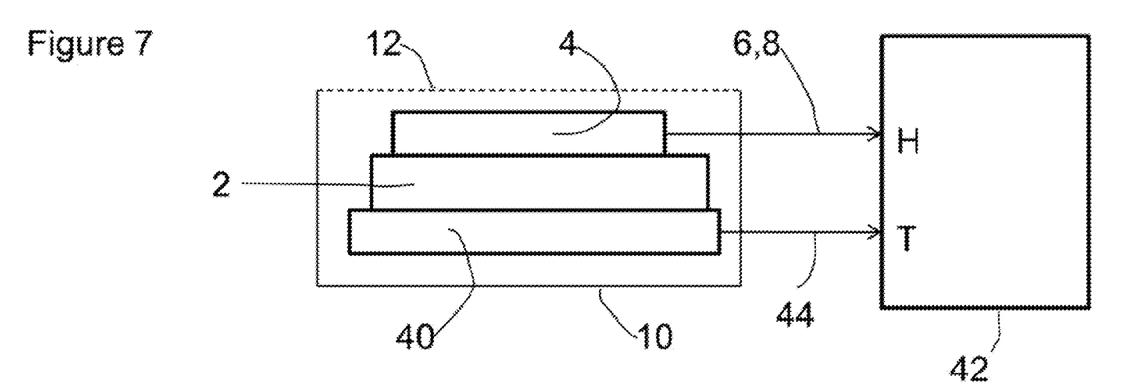
FIG. 7 is a schematic diagram of a temperature compensated humidity sensor in accordance with the invention.

Referring to FIG. 7, a humidity sensor comprises a water vapour sensor 2, 4, 6, 8, 10 as described above in combination with a temperature sensor 40 arranged to sense the temperature of the humidity sensor. A processor 42 determines a measure of relative humidity which may also be compensated for the variation of resistance of the carbon nanotube film with temperature. To compensate for temperature variation, the variation of resistance of a film 4 may be measured as temperature changes but humidity is held constant to determine the equation representing resistance variation with temperature. That equation is used to compensate for the variation of resistance with temperature.

The temperature sensor 40 may be any suitable temperature sensor arranged to sense the temperature of the humidity sensor. In one example the temperature sensor is a platinum based resistor deposited on the substrate 2 immediately adjacent to the film, 4.

In another example the temperature sensor comprises a film of carbon nanotubes impregnated with surfactant (the same as the water vapour sensor) but encapsulated so that the film is unaffected by water vapour. The temperature sensor is in close contact with the water vapour sensor to detect its temperature.

The determination of relative humidity from a measure of temperature and humidity is known in the art and will not be discussed here.

Figure 8:
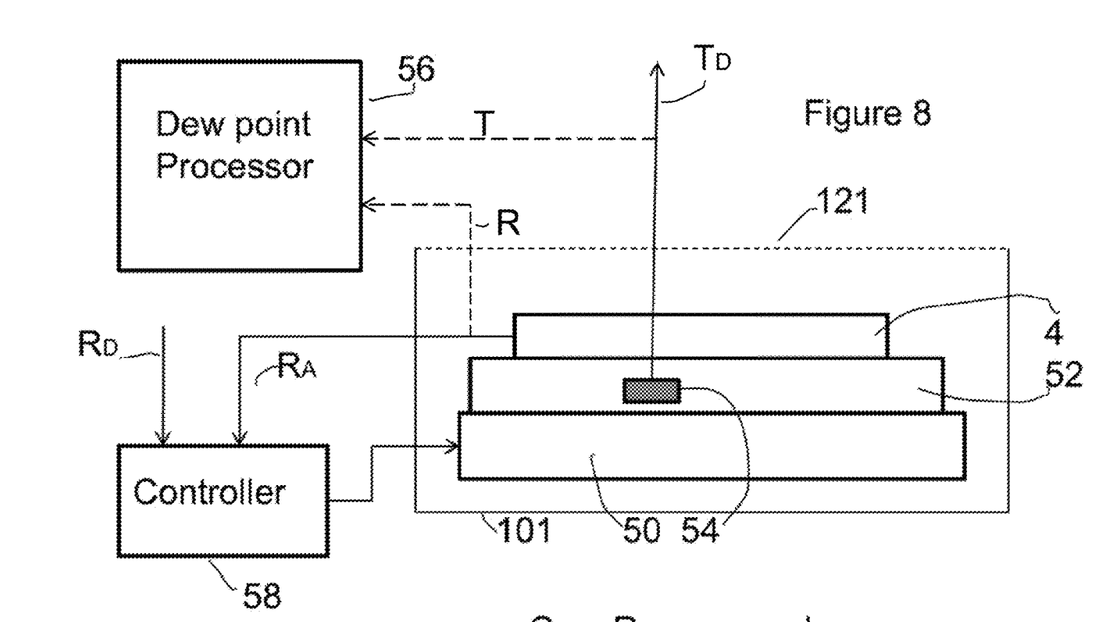
FIG. 8 is a schematic diagram of a dew point sensor including a water vapour sensor in accordance with the invention.

Referring to FIG. 8, the water vapour sensor described hereinabove may be used in a dew point sensor. The dew point sensor of FIG. 8 comprises a cooler, in this example a Peltier cooler 50. The cooler has a cooled face 52, which may be a ceramic substrate. A film 4 of carbon nanotubes impregnated with surfactant, e.g. SDS, may be deposited directly on the cooled face or a sheet of PET carrying the film as described above may be fixed to the cooled face 52. Placing the film directly on the cooled face avoids having any thermal barrier between the film and the cooled face.

A temperature sensor 54 is provided to sense the temperature of the cooled face 52 and the water vapour sensor. In this example the temperature sensor is in contact with, or embedded in, the cooled face 52.

The water vapour sensor and cooler are housed in a housing 101 having a porous face 121 which allows humid air into the housing.

A processor 56 may be provided to determine the dew point D using the sensed temperature T and the humidity measure H provided by the water vapour sensor.

Two ways of determining dew point are described below.

In one way, which does not require the processor 56, as shown in FIG. 8, the dew point sensor comprises a controller 58 which is responsive to (i) a reference value $R_D$ representing a predetermined resistance value (which is the resistance of the film 4 when dew just forms on it) and (ii) the actual measured the resistance $R_A$ of the film, which is kept equal to $R_D$ to maintain the cooled face 54 at the dew point temperature. In an example the film 4 is maintained at a temperature which has a predetermined offset from the dew point. The offset, if used, is chosen to prevent the formation of water droplets on the surface of the carbon nanotube film because water droplets may erode surfactant from the film. The reference $R_D$ may be chosen to provide the offset. The controller acts as the controller of a feedback loop in which the reference $R_D$ (reference dew point resistance) is the reference value and the actual resistance $R_A$ of the carbon nanotube film 4 is the controlled variable, $R_A$, being controlled to equal $R_D$ by varying the cooling of the film. The temperature $T_D$ sensed by the temperature sensor 54 is the dew point or a temperature offset by a predetermined amount from the dew point temperature.

Variations in ambient conditions are tracked by variations in the resistance, $R_A$ of the film 4 and controlling the temperature T of the cooled face to maintain the resistance of the film 4 at the reference dew point resistance $R_D$ or at the predetermined offset from the dew point.

The reference value $R_D$ may be established by cooling the film and observing the surface of the film optically (using for example a microscope) to determine when dew just forms on the surface and measuring the resistance of the film at that point. The measured resistance is the reference value representing the dew point. If the offset is used the value of $R_D$ is adjusted accordingly. The surface of the film may be observed optically by a person using a microscope or it may be observed using a laser and detecting laser light scattered from the surface as in a cold mirror dew point sensor.

A second way, which uses the processor 56, will now be described with reference to FIGS. 9 to 12.

Figure 9:
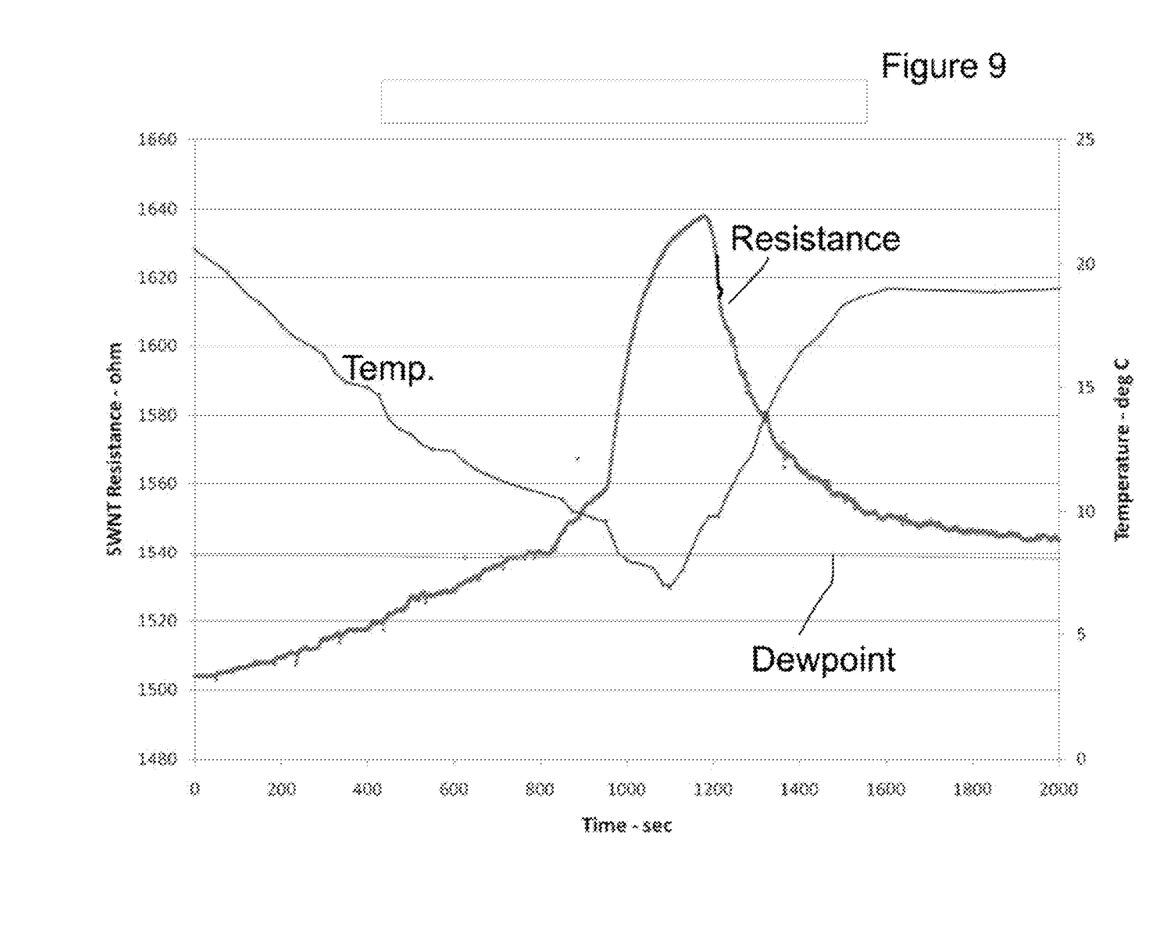
FIG. 9 a graph showing the change of resistance over time with changes in temperature of the sensor of FIG. 8 together with dew point temperature.
Figure 10:
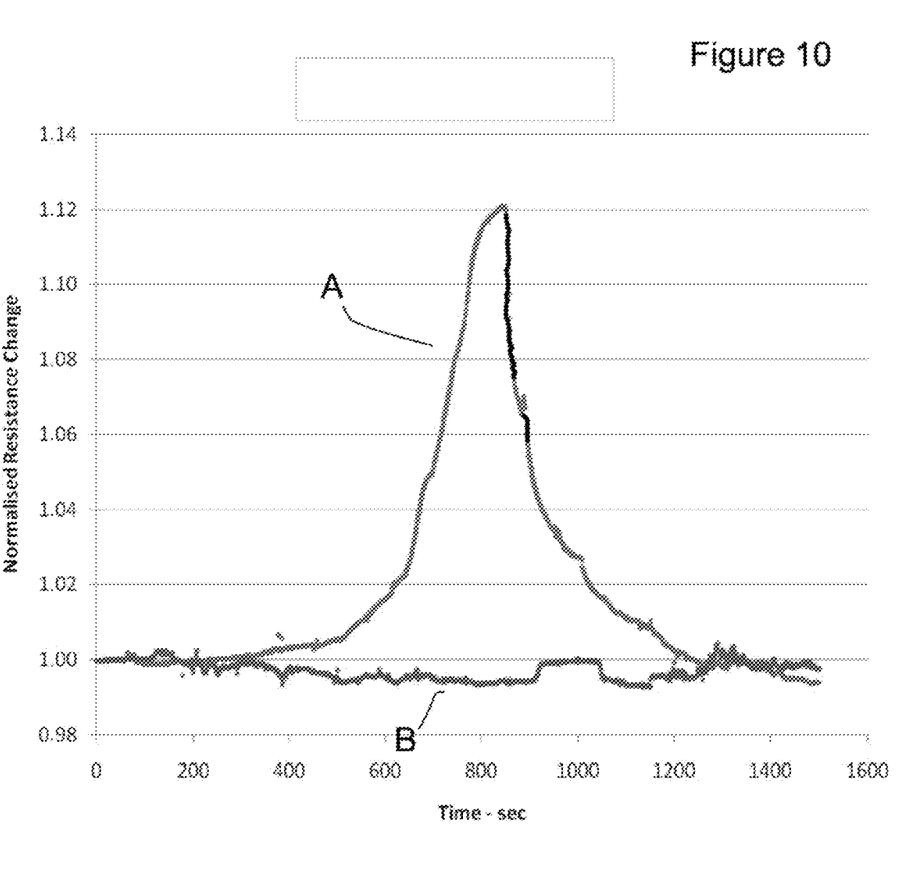
FIG. 10 is a graph comparing the change of resistance of the sensor of FIG. 8 compared to a different form of sensor.

FIG. 9 is a graph of an experimental result using SDS impregnated SWNT film. In the experiment, the SWNT film starts at room temperature and is cooled by the cooler. On cooling, the SWNT film's resistance (Res) initially increases very slowly, but near the dew point the resistance increases rapidly. When the cooling is stopped (by warming the sensor), the film resistance drops equally rapidly, before returning close to its original value. The resistance curve takes on a characteristic 'peaked' profile when SWNT Resistance and Temperature are plotted against time. The line labelled 'Dewpoint', was obtained using a Testo 610 instrument which derives the dew point temperature from its relative humidity measurement. The exact shape of the resistance curve depends on the cooling and heating rates obtaining during the test. Faster rates, produce curves with sharper peaks FIG. 10 is a graph of a comparison of SDS impregnated SWNT film A and washed film (i.e. SDS removed) B. For the normalised curves shown in the graph, the increase in resistance as the sample is cooled (temperature curves not shown, for clarity) to the dew point is almost completely suppressed when the film with the SDS surfactant removed, by washing with deionized water, is tested (curve B).

Figure 11:
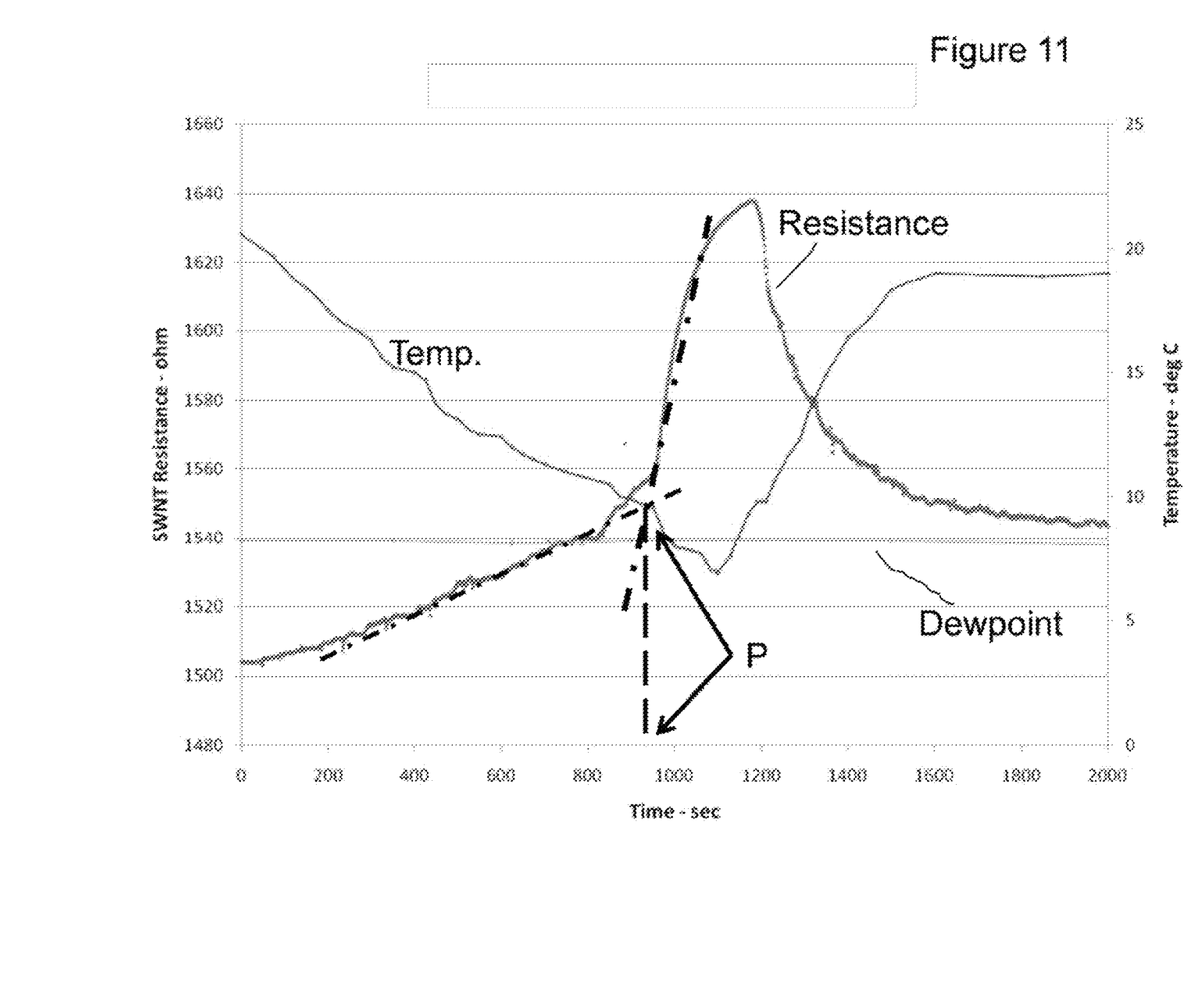
FIG. 11 is a diagram explaining the derivation of dew point using the sensor of FIG. 8.
Figure 12:
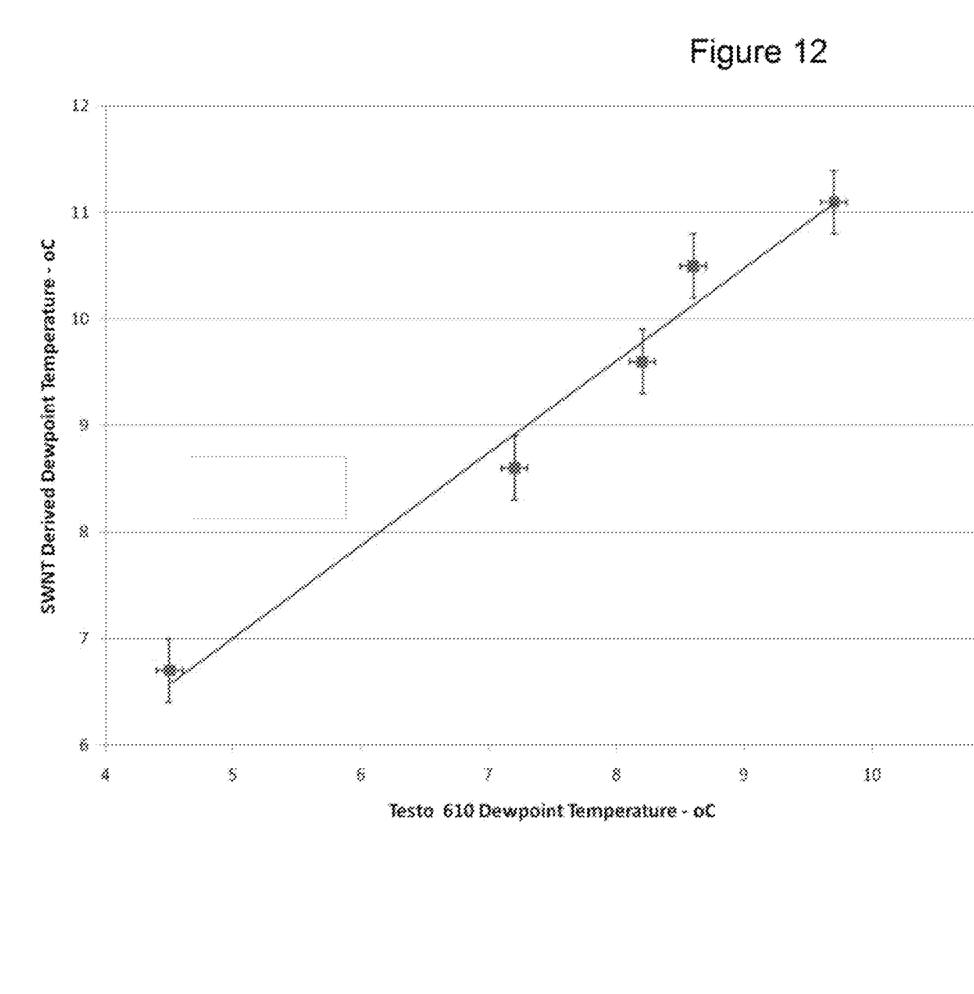
FIG. 12 is a graph comparing results derived from the sensor of FIG. 8 with results from a Testo 610 meter; and, FIG. 13 is a schematic diagram of an alternative humidity sensor in accordance with the invention.

FIG. 11 illustrates a way of determining the actual dew point. This method uses the intersection of straight line fits to the slow and fast changing parts of the SWNT resistance curve. The position P (time and temperature) of intersection of the straight lines is assumed to be the dew point giving the dew point temperature. As shown in FIG. 12 described below the assumed dew point is actually offset from the actual dew point. The processor 56 is programmed to record the variations of resistance R and temperature T as the film is cooled and heated and to fit the straight lines to the resistance curve and to find the intersection of the straight lines.

The method of line fitting described with reference to FIGS. 9, 10 and 11 to derive dew point temperatures and comparing them with readings from a Testo 610 meter, recorded during the same cooling cycle, yields the graph of FIG. 12. The relationship is linear, although the slope and offset indicate that the curve fitting technique does not yield the true dew point temperature, but an offset value. Since the measurement is dependent on the shape of the curves and not the absolute value of resistance, it is robust to erosion of the surfactant when condensation forms on the film surface, as discussed above.

Figure 13:
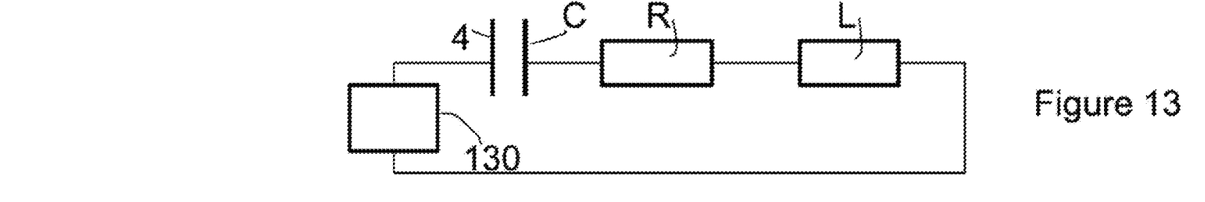

The above embodiments are to be understood as illustrative examples of the invention. Further embodiments of the invention are envisaged. For example, referring to FIG. 13, instead of directly measuring resistance of the carbon nanotube film 4, the film may be part of a resonant circuit and variations in amplitude of a resonant signal may be used as a measure of water vapour sensed by the film 4. In one example the film 4 forms at least one electrode 4 of a capacitor C in an RC or RLC resonant circuit. The resistance of the film which provides at least part of the resistance R in the circuit (and not the capacitance of the capacitor C) varies with the sensed amount of water vapour.

It is to be understood that any feature described in relation to any one embodiment may be used alone, or in combination with other features described, and may also be used in combination with one or more features of any other of the embodiments, or any combination of any other of the embodiments. Furthermore, equivalents and modifications not described above may also be employed without departing from the scope of the invention, which is defined in the accompanying claims.

The invention claimed is:

1. A water vapour sensor comprising:
   a substrate;
   a film of carbon nanotubes impregnated with a surfactant on the substrate, the substrate being inert relative to the film;
   at least two electrical conductors in spaced apart contact with the film to measure a resistance of the film as a measure of humidity; and
   a housing containing the substrate and film, the housing allowing exposure of the film to water vapour.

2. The water vapour sensor according to claim 1, wherein the film includes zones of carbon nanotubes free of surfactant and the electrical conductors contact respective surfactant free zones.

3. The water vapour sensor according to claim 1, wherein the surfactant is sodium dodecyl sulphate, SDBS (sodium dodecyl benzene sulfonate), CTAB (Hexadecyl Trimethyl Ammonium Bromide), or polyethylene glycol p-(1,1,3,3-tetramethylbutyl)-phenyl ether.

4. The water vapour sensor according to claim 1, wherein the carbon nanotubes are single walled tubes.

5. The water vapour sensor according to claim 1, wherein the substrate is of plastics, PET, ceramic, glass, paper or silicon.

6. The water vapour sensor according to claim 1, further comprising a measuring device coupled to the electrical conductors for measuring the resistance of the film as a measure of humidity.

7. The water vapour sensor according to claim 1, wherein the surfactant is sodium dodecyl sulphate (SDS) or sodium dodecyl benzene sulfonate (SDBS).

8. The water vapour sensor according to claim 1, wherein the carbon nanotubes are single walled tubes and the surfactant is sodium dodecyl sulphate (SDS).

9. A humidity sensor for sensing relative humidity comprising:
   a substrate;
   a film of carbon nanotubes impregnated with surfactant on the substrate, the substrate being inert relative to the film;
   at least two electrical conductors in spaced apart contact with the film to measure a resistance of the film as a measure of humidity;
   a housing containing the substrate and film, the housing allowing exposure of the film to water vapour; and
   a temperature sensor arranged to sense a temperature of the film.

10. The humidity sensor according to claim 9, further comprising a measuring device coupled to the electrical conductors for measuring the resistance of the film and to the temperature sensor for determining a measure of relative humidity compensated for the effect of temperature on the film.

11. A dew point sensor comprising:

a cooling device;

a water vapour sensor arranged to be cooled by the cooling device, the water vapour sensor including: a substrate; a film of carbon nanotubes impregnated with surfactant on the substrate, the substrate being inert relative to the film; at least two electrical conductors in spaced apart contact with the film to measure a resistance of the film as a measure of humidity; and a housing containing the substrate and film, the housing allowing exposure of the film to water vapour; and a temperature sensor arranged to sense a temperature of the dew point sensor.

12. The dew point sensor according to claim 11, wherein the film is on a cooled face of the cooling device of the dew point sensor.

13. The dew point sensor according to claim 11, further comprising a measuring device coupled to the water vapour sensor and to the temperature sensor for determining a dew point.

14. The dew point sensor according to claim 11, further comprising a feedback controller responsive to (i) a reference resistance value related in a predetermined manner to the resistance of the film when dew just forms on the film and (ii) the actual resistance of the film to control the cooler to maintain the resistance of the film at the reference resistance, whereby the said sensed temperature is related to the dew point.

* * * * *